(12) United States Patent
Ascher et al.

(10) Patent No.: US 9,011,519 B2
(45) Date of Patent: Apr. 21, 2015

(54) IMPLANTABLE MEDICAL DEVICE INCLUDING A PROTECTION/RETAINING LAYER FOR AN ACTIVE INGREDIENT OR DRUG, IN PARTICULAR A WATER-SOLUBLE ONE

(75) Inventors: Gilles Ascher, Neuilly-sur-Seine (FR); Edoardo Camenzind, Bellinzona (CH)

(73) Assignees: Edoardo Camenzind, Bellizona (CH); Hexacath, Rueil-Malmaison (FR)

( * ) Notice: Subject to any disclaimer, the term of this patent is extended or adjusted under 35 U.S.C. 154(b) by 947 days.

(21) Appl. No.: 12/918,644

(22) PCT Filed: Feb. 20, 2009

(86) PCT No.: PCT/FR2009/050277
§ 371 (c)(1),
(2), (4) Date: Oct. 19, 2011

(87) PCT Pub. No.: WO2009/112741
PCT Pub. Date: Sep. 17, 2009

(65) Prior Publication Data
US 2012/0172794 A1    Jul. 5, 2012

(30) Foreign Application Priority Data

Feb. 21, 2008  (FR) ..................... 08 51135
Feb. 21, 2008  (FR) ..................... 08 51136
Feb. 21, 2008  (FR) ..................... 08 51137
Feb. 21, 2008  (FR) ..................... 08 51138

(51) Int. Cl.
*A61F 2/06*    (2013.01)
*A61L 31/10*    (2006.01)
*A61L 31/16*    (2006.01)

(52) U.S. Cl.
CPC ................. *A61L 31/10* (2013.01); *A61L 31/16* (2013.01); *A61L 2300/114* (2013.01);
(Continued)

(58) Field of Classification Search
USPC ................................. 623/1.42, 1.46
See application file for complete search history.

(56) References Cited

U.S. PATENT DOCUMENTS

| 4,912,093 A | 3/1990 | Michaeli |
| 5,874,419 A | 2/1999 | Herrmann et al. |

(Continued)

FOREIGN PATENT DOCUMENTS

| EP | 0 850 604 | 7/1998 |
| EP | 1 180 903 | 2/2002 |

(Continued)

OTHER PUBLICATIONS

Devesh Kothwala et al, "Paclitaxel Drug Delivery from Cardiovascular Stent," Trends in Biomaterials & Artificial Organs, vol. 19, No. 2, Jan. 2006, pp. 88-92, XP002548439, p. 89, col. 1, Reseach and Development Division, Sahajanand Medical Technologies, Surat—395 003, India, University of Texas at San Antonio, TX 78249.

*Primary Examiner* — Thomas J Sweet
*Assistant Examiner* — Seema Mathew
(74) *Attorney, Agent, or Firm* — Lucas & Mercanti, LLP

(57) ABSTRACT

An implantable medical device (10) comprises reservoirs (30) for receiving a water-soluble active agent or medicament (36) in the form of a solid deposit; and at least one biocompatible and biodegradable protecting/retaining layer (38) for protecting the active agent or medicament (36) until it reaches its site of implantation, said biocompatible and biodegradable protecting layer (38) comprising at least one biocompatible and biodegradable film-forming agent, and at least one hydrophobic, biocompatible, agent for controlling the disintegration rate of the protecting/retaining layer. The invention provides better protection of the active agent or medicament and better control of the disintegration rate of the protecting/retaining layer.

34 Claims, 1 Drawing Sheet

(52) U.S. Cl.
CPC ..... *A61L 2300/406* (2013.01); *A61L 2300/416* (2013.01); *A61L 2300/45* (2013.01); *A61L 2300/604* (2013.01); *A61L 2300/622* (2013.01)

(56) References Cited

U.S. PATENT DOCUMENTS

| | | | |
|---|---|---|---|
| 6,379,381 B1* | 4/2002 | Hossainy et al. | 623/1.42 |
| 6,491,720 B1* | 12/2002 | Vallana et al. | 623/1.42 |
| 6,702,850 B1 | 3/2004 | Byun et al. | |
| 6,994,867 B1 | 2/2006 | Hossainy et al. | |
| 7,044,965 B1* | 5/2006 | Spielberg | 623/1.42 |
| 7,084,117 B2 | 8/2006 | Culler et al. | |
| 7,208,011 B2* | 4/2007 | Shanley et al. | 623/1.42 |
| 7,575,593 B2* | 8/2009 | Rea et al. | 623/1.42 |
| 7,655,038 B2* | 2/2010 | Luthra et al. | 623/1.42 |
| 7,922,760 B2* | 4/2011 | Hossainy | 623/1.42 |
| 8,070,797 B2* | 12/2011 | Flanagan et al. | 623/1.42 |
| 8,137,397 B2* | 3/2012 | Colen et al. | 623/1.42 |
| 8,328,867 B2* | 12/2012 | Dolan et al. | 623/1.42 |
| 8,449,603 B2* | 5/2013 | Weber et al. | 623/1.48 |
| 2002/0082679 A1* | 6/2002 | Sirhan et al. | 623/1.15 |
| 2002/0123801 A1* | 9/2002 | Pacetti et al. | 623/1.46 |
| 2003/0028243 A1 | 2/2003 | Bates et al. | |
| 2003/0060871 A1* | 3/2003 | Hill et al. | 623/1.15 |
| 2003/0069631 A1* | 4/2003 | Stoll | 623/1.15 |
| 2003/0125803 A1* | 7/2003 | Vallana et al. | 623/1.42 |
| 2004/0249449 A1* | 12/2004 | Shanley et al. | 623/1.43 |
| 2005/0010282 A1* | 1/2005 | Thornton et al. | 623/1.42 |
| 2005/0125054 A1* | 6/2005 | Bhat et al. | 623/1.42 |
| 2005/0239743 A1 | 10/2005 | Zomer et al. | |
| 2008/0071355 A1* | 3/2008 | Weber et al. | 623/1.16 |
| 2009/0018646 A1* | 1/2009 | Zhao | 623/1.43 |
| 2009/0099651 A1* | 4/2009 | Hakimi-Mehr et al. | 623/1.42 |
| 2009/0157166 A1* | 6/2009 | Singhal et al. | 623/1.15 |
| 2009/0157172 A1* | 6/2009 | Kokate et al. | 623/1.43 |
| 2009/0259300 A1* | 10/2009 | Dorogy et al. | 623/1.36 |
| 2010/0010621 A1* | 1/2010 | Klocke | 623/1.16 |
| 2010/0057188 A1* | 3/2010 | Weber | 623/1.15 |
| 2010/0057197 A1* | 3/2010 | Weber et al. | 623/1.42 |
| 2010/0131050 A1* | 5/2010 | Zhao | 623/1.42 |
| 2011/0238153 A1* | 9/2011 | Atanasoska et al. | 623/1.15 |
| 2014/0025160 A1* | 1/2014 | Pacetti | 623/1.16 |

FOREIGN PATENT DOCUMENTS

| | | |
|---|---|---|
| EP | 1 277 449 | 1/2003 |
| EP | 1 470 830 | 10/2004 |
| EP | 1 674 117 | 6/2006 |
| WO | 94/22885 | 10/1994 |
| WO | 01/87372 | 11/2001 |
| WO | 2006/067031 | 6/2006 |
| WO | 2006/102359 Y | 9/2006 |

* cited by examiner

IMPLANTABLE MEDICAL DEVICE INCLUDING A PROTECTION/RETAINING LAYER FOR AN ACTIVE INGREDIENT OR DRUG, IN PARTICULAR A WATER-SOLUBLE ONE

This is a National phase of PCT/FR2009/050277 filed Feb. 20, 2009, which claims the priority of FR 08 51135 filed Feb. 21, 2008, FR 08 51136 filed Feb. 21, 2008, FR 08 51137 filed Feb. 21, 2008, and FR 08 51138 filed Feb. 21, 2008, all applications are incorporated by reference herein.

The invention relates to an implantable medical device including a protecting/retaining layer for an active agent or medicament, in particular a water-soluble one.

More specifically, this implantable medical device comprises an active agent or medicament, in particular a water-soluble one, and is characterized in that it comprises at least one protecting and/or retaining layer for protecting/retaining the active agent or medicament until it is at its site of implantation, said layer comprising a biocompatible and biodegradable film-forming agent; and at least one hydrophobic, preferably biocompatible, agent for controlling the degradability rate of the protecting or retaining layer.

In the context of the present invention, in the description and the claims, the following terms have the following meanings:

An active or therapeutically active agent: any agent or product or substance or composition, taken alone or in combination with any other agent, product or substance, which has a therapeutic activity that can prevent or slow down or treat a disease of living beings, in particular humans and animals. It may be used in particular for the prevention or repair of damage caused to a soft tissue or to a bone tissue, for regulating the healing of a wound, for preventing or minimizing the risk of restenosis, or for inhibiting or, on the contrary, promoting angiogenesis.

A medicament or drug is here used indifferently to have the same meaning, and is either an agent or product or substance which, taken alone or in combination with another agent, product or substance, has a therapeutic activity to prevent or slow down or treat a disease, or is a composition comprising at least one of the therapeutically active agents, usually with a pharmaceutically acceptable excipient.

A water-soluble active ingredient or medicament: is an active ingredient or a medicament which is soluble in aqueous medium and in a comparable aqueous medium such as a blood or plasma medium.

A stent: is a prosthesis, placed inside an anatomical cavity (endo-prosthesis) in order to maintain the internal lumen, which is in the form of a tube which has openings in its wall of various types of shapes and sizes or of a mesh generally made of a metal or of another expanding or self-expanding plastically deformable substance.

A film-forming agent: is an agent capable of forming a film.

A biocompatible and biodegradable film-forming agent: is a film-forming agent capable of forming a film which does not generate any tissue reactions and which further can be resorbed and gradually eliminated by the organism.

A hydrophobic agent: is an agent scarcely soluble in an aqueous medium, this hydrophobic agent thus making it possible to adjust the degree of solubility of a biocompatible and biodegradable film or layer in an aqueous medium, and in particular in the blood or plasma. In the context of the present invention, the hydrophobic agent makes it possible to control the disintegration rate of the protecting or retaining layer.

A biocompatible hydrophobic agent means that the hydrophobic agent does not generate any tissue reaction.

In the context of the present invention, the term "biodegradable" means that the protecting/retaining layer disappears at the site of implantation irrespective of the mechanism of action.

The invention provides better protection of the active ingredient or medicament until it reaches its intended destination.

PRIOR ART

Active Ingredients and Delivery Means

Compositions comprising a polyionic derivative of cyclodextrin combined with a growth factor, preferably a heparin-binding growth factor, are known through document U.S. Pat. No. 5,874,419. This composition can be used in a method for inhibiting restenosis according to various routes of administration, one of which comprises the diffusion of an aqueous suspension or dispersion of the saccharide derivative directly into the arterial wall at the site. This solution has the major drawback of being a diffusion of an aqueous suspension or dispersion of the saccharide derivative via a modified infusion balloon catheter, which necessarily implies a diffusion which is limited over time and with virtually instantaneous administration of the active ingredient.

The use of sodium sucrose octasulfate for carrying out an antithrombotic treatment is known from document WO 94/22885, see page 3, line 13.

Document U.S. Pat. No. 4,912,093 discloses, in addition, the use of the same sodium sucrose octasulfate to heal wounds occurring in the skin and bone tissues by using it in the liquid phase or state (claims 6, 8, 9 to 11), or encapsulated in a polymer or the like, see claim 18 of this document.

The article by Mr. Camenzind et al., in Journal of Cardiovascular Pharmacology, volume 43, No. 1, of January 2004, discloses, in addition, the localized intracoronary delivery of octreotide in humans, in the form of a pharmacokinetic study for determining the restenosis-prevention efficacy according to the dose, pages 133 to 138. The octreotide is delivered in the form of a saline solution containing octreotide radiolabeled with $^{111}$In (indium 111) at 0.02 μg per milliliter, infused at a rate of 18 ml per hour so as to achieve a target dose of 0.18 μg in 30 minutes at the site of the angioplasty, by means of an infusion catheter and infused concomitantly with heparin, at a rate of 200 IU/ml. At the end of the article, Mr. Camenzind envisions a delivery by stent, but without giving any technical means for achieving this.

Document US 2005/0239743 A1 discloses, in addition, compositions and methods for inhibiting restenosis, comprising the administration of a restenosis-preventing composition comprising one or more polysaccharides in combination with one or more pharmaceutically active agents, among which is mentioned octreotide (see claims 1 and 5).

The possibility of delivering the composition, by means of an angioplasty device such as a cardiac stent, in the form of a coating is envisioned in this document (page 1, §[0012]), but the description does not give any technical means regarding such a combination with a stent other than the incorporation of the active compounds in polysaccharides such as galactomannans, arabinogalactan, rhamnogalacturonan, carrageenan and locust bean gum (page 1, §[0013]). In vitro tests are carried out on the composition comprising a combination of polysaccharide(s) and of paclitaxel, in order to test the inhibition of smooth muscle cell migration or proliferation.

In addition, document U.S. Pat. No. 7,084,117 discloses pharmaceutical compositions which inhibit vascular proliferation and also a method for the use thereof. This document envisions the use of somatostatin type 1 receptor agonists which can be disposed upon a vascular stent (claim 10). It is indicated that this agonist, termed SSTR-1, would be typically applied at the time of surgery, preferably in a controlled-release formulation and/or using barrier technology.

Furthermore, document EP 1 470 830 from Medtronic Vascular discloses a stent coated with a medicament bound in a polymer comprising a polysulfone/styrene copolymer in block form.

Document U.S. Pat. No. 5,861,168 discloses, in addition, a method for reducing the probability of restenosis resulting from a vascular lesion comprising an NO precursor agent such as L-arginine or L-lysine in the form of an aqueous solution that can be delivered via a catheter (claims 1, 3 and 4).

In addition, U.S. Pat. No. 6,994,867 discloses a composition for inhibiting restenosis which comprises an oligomer L-arginine, L-arginine or an analog, linked through a labile bond to a polymeric matrix (see the claims).

PURPOSES OF THE INVENTION

A main purpose of the present invention is to solve the new technical problem consisting of the provision of a technical solution which makes it possible to administer a therapeutically active agent or a medicament, in particular a water-soluble one, in the form of a solid deposit, while being protected along its route to the site of administration, by a protecting/retaining layer of which, according to a particular embodiment, the disintegration can be advantageously controlled over a given period of time.

A further main purpose of the present invention is to solve this new technical problem according to a technical solution which makes it possible to administer this therapeutically active agent or this medicament according to a usual route of administration, with, if possible, a solution which makes it possible to determine the amount of the active agent or medicament released and/or the period of time over which the active agent or medicament is released, and which is in particular compatible with the use of an implantable medical device, in particular a stent.

A further main purpose of the present invention is to solve the new technical problems mentioned above, according to a technical solution which makes it possible to carry out a restenosis treatment, and especially a vascular restenosis treatment, and in particular at the cardiac level.

All of these technical problems are solved for the first time by the present invention in a safe and reliable manner that can be used on the industrial and medical scale.

DETAILED DESCRIPTION OF THE INVENTION

All of the technical problems mentioned above are solved for the first time by the present invention in a simple, safe and reliable manner which can be used on the industrial and medical scale.

According to a first aspect, the invention relates to an implantable medical device comprising at least one therapeutically active agent or medicament, in particular a water-soluble one, characterized in that it comprises means for receiving said therapeutically active agent or medicament, in the form of a solid deposit; and at least one biocompatible and biodegradable protecting/retaining layer for protecting the therapeutically active agent or medicament until it is at its site of implantation thereof, said protecting layer comprising at least one biocompatible and biodegradable film-forming agent, and at least one hydrophobic, preferably biocompatible, agent for controlling the disintegration rate of the protecting/retaining layer.

The expression "in the form of a solid deposit" means that the agent or the medicament is deposited in the form of a solid deposit or phase on or in the receiving means, in particular so as to form at least one solid layer of said agent or medicament.

According to another optional feature, the biocompatible and biodegradable film-forming agent is selected from a polyalkylene glycol, a polyvinylpyrrolidone, and mixtures thereof in any proportions.

According to yet another optional feature, the polyalkylene glycol comprises or consists of polyethylene glycol.

According to another optional feature, the biocompatible hydrophobic agent comprises dexamethasone or a dexamethasone derivative.

According to yet another particular feature, the dexamethasone derivative comprises dexamethasone, dexamethasone phosphate or dexamethasone acetate.

According to another optional feature, the relative ratio of the biocompatible and biodegradable film-forming agent to the hydrophobic agent varies between 99% and 1% of film-forming agent for 1% to 99% by weight of hydrophobic agent.

According to yet another optional feature, the protecting/retaining layer deposited on the active ingredient or medicament, itself deposited or loaded beforehand onto the above-mentioned receiving means, comprises from 0.1 to 100 µg of dexamethasone component per $mm^2$ of protecting/retaining layer surface.

According to yet another optional feature, the implantable medical device comprises an external surface and said means for receiving said therapeutically active agent or medicament are at least in part located on at least a part of the external surface and in particular can comprise surface sculpturing of the medical device.

In a particular embodiment, the surface sculpturing may comprise reservoir formations defining a predetermined individual reservoir volume for said active agent or medicament, and therefore a predetermined total volume of the individual volumes of the reservoir formations.

According to another particular feature, said reservoir formations can be selected from the group comprising incisions, channels, grooves, wells or cavities.

According to another particular feature, said reservoir formations have a concave or nonconcave, closed bottom.

According to one particular embodiment, the medical device comprises a stent which has an external surface and an internal surface, said means for receiving said active agent or medicament are at least in part located on at least a part of said external surface and comprise surface sculpturing of the stent.

An example of an implantable medical device, which can be a stent, which comprises surface sculpturing, is disclosed in document EP 1 180 903 B1, which is incorporated by reference and from which those skilled in the art can take any useful information. This document shows the forming of reservoirs on the surface of the implantable medical device such as a stent, which may be in the form of incisions or in the form of channels or grooves, and which may have a closed perimeter on the side walls and an open top so as to provide reservoirs for the active agent or medicament applied selectively on the formations. All the formations described and also the method of formation may be used in the context of the present invention.

According to a particular embodiment, it is possible to use, in the context of the invention, any implantable medical device, notably any stent of the prior art, and notably those described in EP 1 180 903 or in EP 1 277 449, said documents also being included by reference. The latter document shows the provision of recesses made on the internal surface of the stent.

Another example of a method for producing stents for angioplasty with surface sculpturing is disclosed in EP 0 850 604 B1, which is also incorporated by reference.

According to another particular embodiment of the invention, it is possible to use an implantable medical device, such as a stent, made of stainless steel or made from an alloy composition, as disclosed in Hexacath prior patent application EP 1 674 117. In particular, the stent may have a passive or alternatively inert additional layer as disclosed in this patent.

According to another particular feature, the implantable medical device, such as a stent, may be provided with a more specific surface sculpturing, comprising the formation, on the external surface of the implantable medical device, at least in part, of microreservoirs, such as microwells or microcavities, having, in a particular embodiment, a hemispherical or ovoid shape or an ellipsoid contour, wherein the bottom of the microreservoirs may be of any shape and notably of concave or noncave, closed shape.

It should be noted that the size, the shape and the number of the microreservoirs, such as microwells or microcavities, determines, firstly, the amount of active agent or medicament loaded and, secondly, the period of time for release thereof.

According to a particular feature, the volume of the network provided by the microreservoirs, i.e. the volume of each microreservoir and therefore the total volume provided, may be controlled, predetermined and defined by three parameters, which can be used individually or in combination.

The volume control parameters comprise:
a) the individual size of the microreservoirs, which may be of micrometric size, notably in the range of between approximately 1 µm and approximately 600 µm, in particular between 10 and 150 µm, with respect to average size;
b) the depth and the shape of the closed bottom of the microreservoirs, the depth being controlled so as to avoid promoting mechanical weaknesses and potential breaks or fractures or cracks in the medical device, notably in the form of a stent;
c) the total number of microreservoirs present on the external surface of the implantable medical device, notably a stent.

Typically, the total number of microreservoirs may be between 1000 and more than one million on a given implantable medical device.

With such a total volume of the network of microreservoirs, such as microcavities or microwells, as defined above or in the description which follows, taken as a whole, the amount of a therapeutically active agent or of a medicament, present in the form of a solid deposit in the cavities or wells of the surface sculpturing and according to the present invention, may vary from 0.1 µg to more than 1 g, depending notably on the physical and chemical characteristics of the therapeutically active agent or of the medicament deposited.

According to a particular embodiment, the total number of microreservoirs made on the apparent surface of the implantable stent may be between 100 and 15000 on a stent having a length of approximately 16 mm.

The method for producing the microreservoirs, such as microwells or microcavities, is well known to those skilled in the art and can result from the previous documents of the prior art revealing surface sculpturing of a stent. Any new surface sculpturing is of course included in the context of the invention.

According to yet another optional feature, the stent comprises a substrate and at least one ceramic coating layer optionally with at least one intermediate, nonporous metallic adhesion layer, as is disclosed in prior document EP 1 674 117 from the applicant.

According to yet another optional feature, a biocompatible and biodegradable protecting and/or retaining layer is deposited on the external surface, in the form of a solid deposit, in said microreservoirs, on top of said active agent or medicament, which is itself present beforehand in a solid form or phase, in order to provide it with protection until it is at its site of implantation, and also to provide the release of said active agent or medicament in the vicinity of the implanted site.

Those skilled in the art understand that the protecting layer is sufficiently resistant to disintegration during the implantation of the medical device until it is at the site of implantation, so that this protecting layer essentially prevents loss of the active ingredient until it is at the site of implantation, the medicament or active agent depositing in the microreservoirs in the form of a solid deposit thus remaining protected until it is at the site of implantation of the medical device. After the medical device has been implanted and direct contact has been obtained between the medical device and the surrounding tissues, the medicament or active agent is locally bioavailable. For a stent, after deployment in the anatomical structure treated, the medicament or active agent, present in the microreservoirs arranged on the external surface of the device, is locally bioavailable. The anatomical structure treated consists of the wall of a blood vessel, a soft tissue or a bone tissue. When the structure treated consists of a blood vessel wall, after deployment of the stent, access of the blood flow to the external surface of the stent and in the microreservoirs containing the active ingredient or the medicament is greatly limited.

According to a first particular embodiment, the medicament or active agent, in particular a water-soluble one, present in the form of a solid deposit, comprises a cicatrization-promoting agent, in the form of a solid deposit, in an effective amount to induce cicatrization/healing of injured tissues in the vicinity of the implanted medical device.

According to a particular variant embodiment, this device is characterized in that the cicatrization-promoting agent comprises or consists of a nonreducing saccharide or a sulfated analog thereof.

According to another particular variant embodiment, the cicatrization-promoting agent comprises or essentially consists of a nonreducing disaccharide or a sulfated analog thereof.

According to yet another particular variant embodiment, the cicatrization-promoting agent comprises or essentially consists of sucrose or a sulfated analog thereof.

According to another particular variant embodiment, the cicatrization-promoting agent comprises or essentially consists of a monosaccharide or a sulfated analog thereof.

According to yet another particular variant embodiment, the cicatrization-promoting agent comprises or essentially consists of glucose or a sulfated analog thereof.

According to another particular variant embodiment, the cicatrization-promoting agent comprises or essentially consists of fructose or a sulfated analog thereof.

According to a particular feature of the invention, the abovementioned sulfated analog is in the form of a salt selected from a sodium salt, a potassium salt, and mixtures thereof.

According to a particular exemplary embodiment, the cicatrization-promoting agent comprises or essentially consists of sodium sucrose octasulfate.

According to another particular embodiment of the invention, which is completely independent of the preceding embodiment, but which can also be combined with said embodiment, the device according to the invention is characterized in that the active agent or medicament, in particular a water-soluble one, (36) comprises at least one inhibitor of growth factors, such as IGFs, in the form of a solid deposit.

According to a particular variant embodiment of the invention, the growth factor inhibitor comprises octreotide, in the form of a solid deposit.

According to yet another particular embodiment of the invention, which is completely independent of the preceding embodiments, but which can also be combined therewith, the device according to the invention is characterized in that the active agent or medicament, in particular a water-soluble one, (36) comprises an NO precursor agent, in solid form.

According to a particular variant embodiment of the invention, the NO precursor agent is chosen from L-arginine, L-lysine and mixtures thereof.

According to yet another particular embodiment of the invention, the device is characterized in that it comprises at least one additional therapeutic agent, in particular an anti-restenosis agent.

According to a particular variant embodiment, the anti-restenosis agent is selected from a medicament inhibiting smooth muscle cell proliferation, a cytoskeletal inhibitor, and a macrocyclic triene antibiotic. This anti-restenosis agent may be water-soluble or water-insoluble. As an example of a water-soluble anti-restenosis agent, the latter may belong to the peptide family, whereas an example of a water-insoluble medicament is a medicament belong to the limus family.

Each of these anti-restenosis agent is well known to those skilled in the art and is not therefore necessary to detail them.

Technical Features of the Protecting and/or Retaining Layer:

The protecting and/or retaining layer constitutes a film system controlling the protecting/retaining of one or more water-soluble active agent(s) or medicament(s) in the context of implantable medical devices, among which mention may be made of implants such as coronary implants, and notably stents, which can comprise surface sculpturing (microsculpturing).

In addition, during the process for implanting these implantable medical devices, for example a stent, an implant or a prosthesis, and in particular during the phase of moving up to the site of implantation, this protecting/retaining layer makes it possible to protect and avoid loss of active agent taken along with said implantable device. Thus, the retention of the active agent is effective until the site of an implantation is reached and therefore makes it possible to guarantee and control the delivery of the amount of active agent or medicament.

According to an optional particular feature, a "microsculpture" implantable device, notably a microsculpture stent, may be used. The term "microsculpture" means the production of microsculptures such as cavities, wells or grooves at the surface, notably external surface, of the implantable medical device, making it possible to load a controlled mass or volume of active agent or medicament. The purpose of the microstructure is also to protect the active agent during the implanting of the medical device or during the deployment of the stent, avoiding any loss of the active agent before affixing against the wall of the anatomical structure, for example the wall of a blood vessel such as an artery. Such an implantable medical device may be made of various "biocompatible" materials well known to those skilled in the art, for example of 316L stainless steel, or of nitinol, which can be coated with one or more layers for improving the mechanical properties, as disclosed in prior document EP 1 674 117 by the applicant.

The Elements Constituting the Retaining Layer:

The retaining layer is constituted of one or more biocompatible and bioresorbable film-forming agents and of a hydrophobic agent, preferably a biocompatible one, making it possible to delay the disintegration of the retaining layer.

Film-Forming Agents:

The biocompatible and biodegradable film-forming agent can be selected from a polyalkylene glycol, a polyvinylpyrrolidone and mixtures thereof in any proportions.

The polyalkylene glycol may be polyethylene glycol, in particular polyethylene glycol 8000.

The biocompatible and bioresorbable film-forming agent has a concentration in the film forming the protecting/retaining layer of greater than 1% by weight if it is the only film-forming agent constituting the retaining layer.

The use of any other biocompatible and bioresorbable polymer of the glycol family is possible, likewise any combination of these glycol polymers that may ultimately result in a copolymer.

A biocompatible and bioresorbable polymer such as Poly-VinylPyrrolidone PVP (CAS number: 9003-39-8) can also be used as film-forming agent of the protecting/retaining layer. In addition, a combination of film-forming agent based on glycol polymer and on PVP may also be used.

Agents for Delaying the Disintegration of the Protecting/Retaining Layer:

In order to delay the disintegration, in particular the crumbling and/or the dissolution, of the protecting/retaining layer for the active agent or medicament, a hydrophobic agent, preferably a biocompatible one, or a mixture of agents, at least one of which is hydrophobic, will be used. As hydrophobic agent, use will in particular be made of dexamethasone or a derivative thereof, which is very sparingly soluble in an aqueous medium. Dexamethasone is an agent which makes it possible to efficiently delay the disintegration of the retaining layer.

The dexamethasone agent is biocompatible. In addition, all dexamethasone derivatives having a relative hydrophobicity, such as, for example, the disodium salt of dexamethasone phosphate (CAS No. 2392-39-4) or dexamethasone acetate (CAS No. 1177-87-3) can be used as an agent for delaying the disintegration of the protecting/retaining layer.

Those skilled in the art will understand that all the candidates eligible as agent for delaying the disintegration of the protecting/retaining layer should give the protecting/retaining layer a relative hydrophobic agent and should preferably have an acknowledged innocuousness in this type of application and preferably a long-established biocompatible nature.

Depositing Mode:

The depositing of the protecting/retaining layer at the surface of the implantable medical device may be carried out by any technique known to those skilled in the art, for instance by vaporization, nebulization or spraying, such as the "air spray" technique, by ultrasonic vaporization, nebulization or spraying, or by means of any other system that can deposit films by nebulizing or spraying solutions.

The depositing of the protecting/retaining layer may also be performed by the "jetting" technique. This "jetting" technique, which is well known to those skilled in the art, is directly derived from the "ink-jet deposition" techniques.

The protecting/retaining layer can also be prepared by means of a "dipping" technique.

There is no need to describe all these techniques in greater detail since they are well known to those skilled in the art.

Composition of the Protecting/Retaining Layer:

The physicochemical characteristics of this layer or of this film control its disintegration over time when the film is subjected to aqueous, serum, plasma and/or blood conditions.

Lists of Constituent Elements, Roles and Compositions of the Retaining-Elution Layer:

To do this, the current best mode of preparation of the protecting/retaining layer is given hereinafter. It is apparent for those skilled in the art that other film-forming agents or agents for delaying the rate of disintegration of the retaining layer can be used in an equivalent manner.

| Component | Main role | Secondary role | Composition in the film |
|---|---|---|---|
| PEG 8000 | Film-foming agent | Bioavailability agent | >1% by weight |
| Dexamethasone | Agent for delaying the rate of disintegration of the retaining layer | No activity owing to amount being too small | 1% to 99% by weight 0.1 to 100 microg/mm$^2$ of protecting/ retaining layer surface |
| Water | Solvents | Modification of the surface tension of the deposited film | 0-15% by volume |
| Methanol | | | 40-100% by volume |
| Ethanol | | | 0-20% by volume |
| Isopropanol | | | 0-40% by volume |
| Butanol and/or isobutanol | | | 0-40% by volume |

Performance levels, retaining film hold time: from 1 to 45 minutes.

Thickness of the protecting/retaining film: 0.1 to 20 µm.

According to a particular embodiment, from 40% to 70% by weight of hydrophobic agent and from 60% to 30% by weight of film-forming agent can be envisioned in the protecting/retaining layer.

Thickness of the Protecting/Retaining Layer and Possible Number of Sublayers:

It is in general desirable for the total thickness of the protecting/retaining layer not to be too great. This is because too great a thickness could modify the profile and reduce the navigability of the implantable medical device, such as a stent. It is generally desirable for the total thickness of the protecting/retaining layer not to exceed 20 micrometers (microns).

The simplest case is that the protecting/retaining layer is composed of a single layer having a given thickness and a given composition.

However, as required, it is possible to envision the case where the protecting/retaining layer is composed of several protecting/retaining sublayers having varying thicknesses and varying compositions. The total thickness of the protecting/retaining layer is then the sum of the thicknesses of the various sublayers of which it is constituted.

Distribution and Concentration of Agent for Delaying the Disintegration of the Protecting/Retaining Layer:

The total concentration of agent for delaying the disintegration of the protecting/retaining layer is fixed by the total mass of this agent relative to the total mass of the protecting/retaining layer.

The agent for delaying the disintegration of the protecting/retaining layer can be distributed homogeneously or uniformly over the entire thickness of the protecting/retaining layer. In this case, the retaining force or the rate of disintegration or of disappearance (reduction in thickness) of the protecting/retaining layer is constant over the entire thickness of the protecting/retaining layer.

For some needs, it is possible to obtain a protecting/retaining force which can vary according to the thickness of the retaining layer. This is referred to as obtaining a protecting/retaining force gradient. In order to produce this protecting/retaining force gradient, the concentration of the agent for delaying the disintegration of the protecting/retaining layer varies according to the thickness of the protecting/retaining layer. Thus, in a "monolayer" protecting/retaining layer, a gradient of the concentration of the agent for delaying the disintegration of the protecting/retaining layer, over the entire thickness, will make it possible to obtain a retaining force gradient in said layer.

A similar result can be obtained by combining several retaining sublayers having different compositions and different thicknesses. The retaining-force gradient will be the result of the retaining forces of the various individual sublayers.

The protecting/retaining layer may be discontinuous, covering only the active ingredient(s) or medicament(s) present beforehand in the microreservoirs of the medical device of the stent.

Thus, it is understood that the retaining force of the protecting/retaining layer is adjusted so as to essentially prevent any loss of the active ingredient or medicament during the journey made by the medical device to its final position at the site of implantation Roles of the Solvents:

The solvents used are not part of the composition of the protecting/retaining layer since they are completely evaporated off so as to obtain the "dry" protecting/retaining layer said to be in the solid state or phase. However, the use of a mixture of solvents makes it possible to modify virtually on demand the parameters for depositing the protecting/retaining layer, such as the homogeneity, the distribution, the thickness, the drying time, etc.

Method of Treatment

According to a second aspect, the present invention also relates to a method of treating a human or animal individual needing said treatment, comprising the provision of an implantable medical device as defined in the present description and the claims, and the implantation of this implantable medical device at the appropriate place in said individual, in order to carry out the appropriate treatment.

This appropriate treatment may be a medical treatment with at least one active agent or one medicament of which a local action is desired at the site of implantation. This active agent or this medicament can be used for preventing or repairing damage caused to a tissue or to a bone, for regulating the cicatrization of a wound, for preventing or minimizing the risk of restenosis, or for inhibiting or, on the contrary, promoting angiogenesis.

Those skilled in the art will readily understand that the invention can be used for carrying out various treatments in an individual.

Other purposes, features and advantages of the invention will become clearly apparent in the light of the explanatory description which follows, making reference to several examples or embodiments of the invention given simply by way of illustration and which cannot in any way limit the scope of the invention.

In the examples, all the percentages are given by weight, the temperature is in degrees Celsius and the pressure is atmospheric pressure, unless otherwise indicated.

EXAMPLES OF THE INVENTION

Example 1

Figure 1:
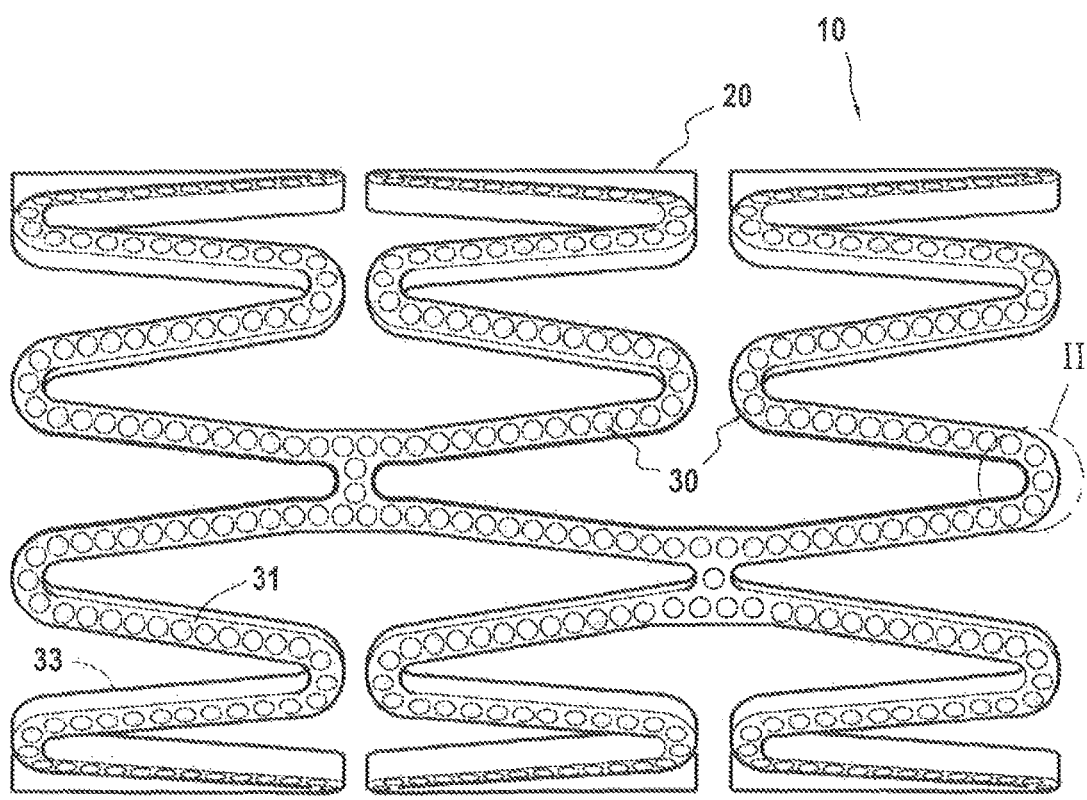
FIG. 1 shows a first embodiment of an implantable medical device, and in particular here a stent, with an external surface comprising surface sculpturing.
Figure 2:
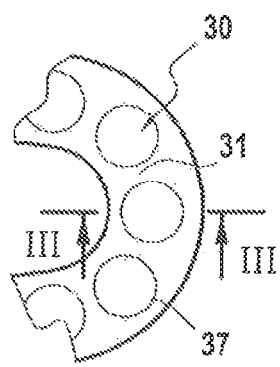
FIG. 2 shows an enlarged view according to the region of arrow II of FIG. 1, of a curved part of the implantable medical device, in particular here a stent, on top of the external surface in order to see the surface sculpturing more clearly.
Figure 3:
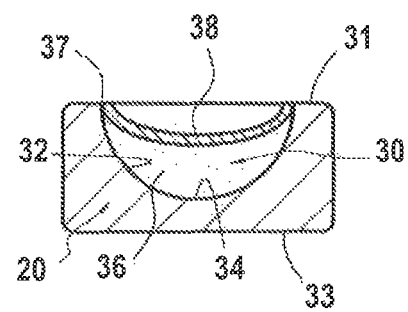
FIG. 3 shows a further enlarged view of a transversal cross section along cutting line III-III of FIG. 2 of a microsculpture, here a microreservoir 30, such as a microwell or a microcavity with a concave closed bottom and in order to show the solid deposit of medicament(s) and also the external solid protecting/retaining layer, inside said microsculpture, here a microreservoir.
Figure 4:
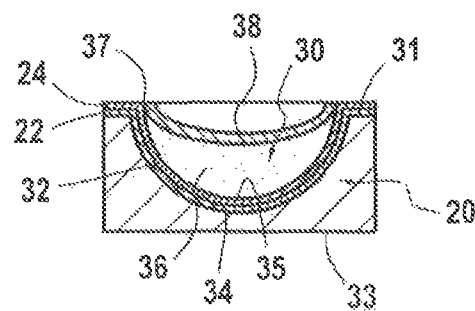
FIG. 4 shows an enlarged view similar to FIG. 3 of a variant embodiment wherein the stent structure comprising a substrate 20 and at least one ceramic coating layer 22 with, optionally, at least one intermediate, nonporous, metallic adhesion layer 24, as disclosed in EP 1,674,117.

Preparation of an Implantable Medical Device, in Particular a Stent, with an External Surface Comprising Surface Sculpturing In reference to FIG. 1, the example taken is an implantable medical device 10, for example here a stent 20, made of 316L stainless steel or 316L stainless steel coated with at least one transition layer, notably of titanium oxynitride, as described in previous Hexacath patent EP 1 674 117.

The device 10, such as a stent 20, comprising an external surface 31, intended to come into contact with the internal tissues of an individual, in particular a blood vessel, and an internal surface 33, was subjected to the formation of surface sculpturing in order for it to comprise reservoir formations 30 defining a predetermined reservoir volume for an active agent or medicament to be deposited therein in a solid phase or state, as described hereinafter in example 2.

The formation of said surface sculpturing was envisioned in particular in this example in the form of multiple reservoirs 40 30 of micro size having a microwell or microcavity shape with one or more side walls 32 and a bottom wall 34, here substantially hemispherical in shape, and also an upper opening 37.

The method of obtaining this type of surface microsculpturing by micro patterning, electrochemical machining or photoelectrochemical machining techniques is well known for those skilled in the art.

The various steps which made it possible to obtain this type of microsculpturing of a stent of this example 1 are the following:

Step 1: The starting platform of a stent, preferably a stent of the Helistent® brand made of 316L stainless from the company Hexacath, France.

Step 2: Microsculpture preparation

A protecting lacquer of cataphoretic type is deposited on the stent in a controlled manner.

A network of hemispherical imprints is created on the external surface of the stent, on the surface of the deposited lacquer, by means of a laser ablation technique well known to those skilled in the art.

Step 3: A network of microsculptures in the form of microreservoirs, such as microcavities or microwells, is created.

The network of microsculptures in the form of microreservoirs, such as microcavities or microwells, is created by means of a technique of electrochemical machining in an acidic medium. The size of these microreservoirs is directly linked to the electrochemical machining time. For example, a stent having a length of 16 mm, and more particularly a stent of the Helistent® brand from Hexacath can have 2900±1% hemispherical microreservoirs having a given diameter corresponding to a desired controlled volume.

In this exemplary embodiment, the average diameter of the hemispherical microreservoirs 30 is approximately 65 µm, the depth is approximately 32 µm on average and the total volume of all the hemispherical microcavities is approximately 0.2 microliters (µl).

It is understood that the formation of these reservoirs makes it possible to deposit, inside said reservoirs, at least one layer, in the solid form or state, of one or more active agent(s) or medicament(s), as given, for example, in example 2 hereinafter, by way of illustration.

Example 2

Depositing of an Active Agent or Medicament in the Form of at Least One Layer in the Solid State, Such as L-Arginine, on a Microsculpture, Stent A deposit in the form of a layer in the solid state (36) of L-arginine was formed inside the microsculptures or the microreservoirs of the stent as described in example 1 above, for example by carrying out the various technical steps that follow:

Step 1: Cleaning of the microsculpture stent, described in exemplary embodiment 1, in a detergent medium together with ultrasound, with finishing by means of hot air or an organic solvent in vapor phase.

Step 2: Low-pressure plasma surface activation with an oxidizing reactive atmosphere. For example, this activation of the surface was carried out using a commercially available Diener Electronic-brand machine, model Femto 3. An example of low-pressure plasma activation conditions is treatment for 10 minutes in plasma with oxygen as gas, at a pressure of 0.50 mbar and a power of 75 watts.

Step 3, filling the microreservoirs with active agent.

Various techniques such as dipping or spraying (air spray, ultrasonic spray or other technique for vaporizing or nebulizing of solution) or ink-jetting can be used to specifically perform the filling of the microreservoirs of the stent.

Technical conditions satisfactory for filling the microreservoirs 30, here microcavities, are air-spraying of an aqueous solution with 15% by volume of isopropyl alcohol containing 20% by volume of L-arginine.

Thus, the aqueous solution of L-arginine was vaporized onto the device 10 such as a stent 20, as obtained in example 1, with the reservoirs of micro size 30, so as to form a layer of solid deposit 36 of the active agent or medicament comprising L-arginine, on the internal surfaces 32-34 of the reservoirs which have the shape of hemispherical microwells or microcavities.

The amount of L-arginine deposited in the microreservoirs 30, such as microwells or microcavities, was well controlled by the total volume thereof and also by the proportion of L-arginine in the solution used for the solid deposit thereof.

Example 3

Depositing of an Active Agent or Medicament in the Form of a Layer, in the Solid State, of a Cicatrization-Promoting Agent for Example a Nonreducing Saccharide, or Else for Example Sodium Sucrose Octasulfate, in the Microstructures or Microreservoirs A deposit in the form of a layer in the solid state (36) of a cicatrization-promoting agent, for example sodium sucrose octasulfate, was formed inside the microsculptures or microreservoirs of the stent as described in example 1 above.

For this, the promotion/cicatrization agent is dissolved in a proportion of 30% by weight in water or in an aqueous medium containing 10% by volume of isopropyl alcohol. Next, the solid deposit is itself produced by means of the various technical steps that follow:

Step 1: Cleaning of the microsculpture stents, described in exemplary embodiment 1, in a detergent medium together with ultrasound, with finishing by means of hot air or an organic solvent in vapor phase.

Step 2: Low-pressure plasma surface activation with an oxidizing reactive atmosphere. For example, this surface activation can be carried out using a commercially available Diener Electronic-brand machine, model Femto 3. An example of low-pressure plasma activation conditions is a treatment for 10 minutes in plasma with oxygen as gas, at a pressure of 0.50 mbar and a power of 75 watts.

Step 3: Filling the microreservoirs with active agent or medicament. Various techniques such as dipping or spraying (air spray or ultrasonic spraying or other techniques for vaporizing or nebulizing a solution) or ink-jetting can be used to specifically carry out the filling of the microreservoirs of the stent.

Technical conditions satisfactory for the filling of the micro-reservoirs 30 are air-spraying of an aqueous solution with 15% by volume of isopropyl alcohol containing 30% by weight of cicatrization-promoting agent, for example sodium sucrose octasulfate.

Thus, the aqueous solution containing the cicatrization-promoting agent is vaporized onto the device 10 such as a stent 20, as obtained in example 1 with the reservoirs 30, so as to form a layer of solid deposit 36 of the active agent or medicament comprising the cicatrizing agent, on the internal surfaces 32-34 of the reservoirs which here have the shape of hemispherical microwells or microcavities.

The amount of cicatrizing agent deposited in the microreservoirs 30 is well controlled and defined by the total volume thereof, and also by the proportion of the cicatrizing agent in the solution used for the solid deposit thereof.

Example 4

Depositing of an Active Agent or Medicament in the Form of at Least One Layer in the Solid State, Such as a Growth Factor-Inhibiting Agent, in Particular Octreotide, on a Microsculpture Stent The depositing of an active agent or medicament, in the solid form or state (36), comprising a growth factor-inhibiting agent, in particular octreotide, on a microsculpture stent as described in example 1 above, is carried out, for example, by implementing the various technical steps that follow:

Step 1: Cleaning of the microsculpture stent, described in exemplary embodiment 1, in a detergent medium together with ultrasound, with finishing by means of hot air or an organic solvent in vapor phase.

Step 2: Low-pressure plasma surface activation with an oxidizing reactive atmosphere. For example, this surface activation can be carried out using a commercially available Diener Electronic-brand machine, model Femto 3. An example of low-pressure plasma activation conditions is a treatment for 10 minutes in plasma with oxygen as gas, at a pressure of 0.50 mbar and a power of 75 watts.

Step 3: Filling the microreservoirs 30 with active agent.

Various techniques such as dipping or spraying (air spray or ultrasonic spraying or other techniques for vaporizing or nebulizing a solution) or ink-jetting can be used to specifically carry out the filling of the microreservoirs of the stent.

Technical conditions satisfactory for filling the reservoirs 30, here microreservoirs, are air-spraying of an aqueous solution with 15% by volume of isopropyl alcohol containing 10 mg/ml of octreotide.

According to a first embodiment, the aqueous solution of a growth factor-inhibiting agent, here octreotide, is vaporized onto the device 10 such as a stent 20, as obtained in example 1 with the reservoirs of micro size 30, so as to form a solid deposit 36 of the active agent or medicament, in this case a growth factor-inhibiting agent, here octreotide, on the internal surfaces 32-34 of the reservoirs 30 which here have the shape of hemispherical microwells or microreservoirs.

The amount of growth factor-inhibiting agent, in particular octreotide, deposited in the microreservoirs 30 is well controlled by the total volume thereof, and also by the proportion of growth factor-inhibiting agent, here octreotide, in the solution used for the solid deposit thereof.

According to a second embodiment, this aqueous solution of a growth factor-inhibiting agent, here octreotide, is deposited selectively inside the microreservoirs 30, as obtained in example 1, of the implantable medical device 10, here an intravascular stent 20, so as to obtain a solid deposit 36 of the active agent or medicament, in this case a growth-factor inhibiting agent, here octreotide, on the internal surfaces 32-34 of the reservoirs which here have the shape of hemispherical microreservoirs, for example by means of the abovementioned "ink-jetting" technique.

In addition, this solid deposit was obtained by means of a microdrop-generating module based on the principle of the "drop on demand" technology known to those skilled in the art. Preferably, a given number of microdrops having a diameter of 60 μm (micrometers) and a volume of 0.1 nL (nanoliter) were deposited selectively in the microreservoirs 30 of the implantable medical device 10, here an intravascular stent 20, as obtained in example 1.

Example 5

Depositing of a Solid External Protecting/Retaining Layer which is Preferably Biocompatible and Biodegradable A biocompatible and biodegradable external layer 38 was additionally deposited on the implantable medical device 10, as obtained in example 2, provided with a medicament here comprising L-arginine, or as obtained in example 3 comprising a cicatrization-promoting agent, or else as obtained in example 4 comprising a growth factor-inhibiting agent, in particular octreotide, in the following way:

A solid external protecting/retaining layer 38 was formed by first of all preparing a solution at 50% by weight of film-forming agents comprising commercially available polyethylene glycol 8000; 50% by weight of dexamethasone, as hydrophobic agent; the whole solubilized in a mixture of solvents comprising, for example, 40%-100% by volume of methanol and 0 to 40% by volume of butanol.

According to a first specific embodiment, this solution was air-sprayed onto the implantable medical device 10, here an intravascular stent 20, comprising the medicament, L-arginine, as obtained in example 2; or a cicatrization-promoting medicament as obtained in example 3; or else a medicament comprising a growth factor-inhibiting agent, in particular octreotide, as obtained in example 4, so as to obtain a solid external protecting/retaining layer having a thickness of between 0.1 and 20 μm. A protecting/retaining layer having a given composition and a given thickness was deposited, for example by means of the abovementioned nebulization/spraying technique.

In addition, this retaining layer was obtained by means of a standard, commercially available nebulization/air-spraying system. Preferably, the model used is a Badger, airbrush, model 150™ (No. WE-150-4 PK) with nozzle sizes M and L. This Badger 150™ was coupled to a WE-Atlantis membrane air compressor, model TF 368, 220 volts and 135 watts.

Owing to the essentially instantaneous vaporization of the solution and to the very low solubility of the active agent or medicament, in this case L-arginine or a cicatrization-promoting medicament as defined in example 3, there was no appreciable disintegration of the active ingredient or medicament during the formation of the solid external protecting/retaining layer.

According to a second specific embodiment, this solution could be deposited selectively on the microcavities 30 comprising the abovementioned medicament, of the implantable medical device 10, here an intravascular stent 20, so as to obtain a solid external protecting/retaining layer 38 having a thickness of between 0.1 and 20 μm. A protecting/retaining layer having a given composition and a given thickness was deposited, for example by means of the abovementioned "ink-jetting" technique.

In addition, this retaining layer was obtained by means of a microdrop-generating module based on the principle of the "drop on demand" technology known to those skilled in the art. Preferably, a given number of microdrops having a diameter of 60 μm (micrometers) and a volume of 0.1 nL (nanoliter) were deposited selectively on the microcavities 30 comprising the abovementioned medicament, of the implantable medical device 10, here an intravascular stent 20, so as to obtain a solid external protecting/retaining layer 38 having a thickness of between 0.1 and 20 μm.

Owing to the essentially instantaneous evaporation of the solution and to the very low solubility of the active agent or medicament, in this case L-arginine, or the cicatrization-promoting medicament, as obtained in example 3, or else the medicament comprising a growth factor-inhibiting agent, and in particular octreotide, as obtained in example 4, there was no appreciable disintegration of the active agent or medicament during the formation of the solid external protecting/retaining layer.

Example 6

Supplementary Tests

Various examples of protecting/retaining layers 38 were carried out. These various examples illustrate some variations in hold and therefore variations in retaining force under given in vitro conditions. Given in vitro conditions common to these various examples:

Working medium No. 1: PBS phosphate buffer at a pH of 7.4
Working medium No. 2: porcine plasma at pH 7.4
Working medium volume: 50 ml
Working medium temperature: 37° C.±0.5° C.
Nonlaminar forced convection system.

Depositing of the Protecting/Retaining Layer on an Implantable Medical Device

A protecting/retaining layer 38 having a given composition and a given thickness was deposited, for example by means of the abovementioned nebulization/spraying technique, on a given surface, for example an implantable medical device 10, such as a stent 20, made of 316L stainless steel or stainless steel coated with a layer of titanium oxynitride biocompatible ceramic, according to the prior Hexacath patent EP 1 674 117 or WO2006/067031, by the applicant.

In addition, the various thicknesses of the retaining layers, of the exemplary embodiments mentioned below, were obtained by means of a standard, commercially available nebulization/air-spraying system. Preferably, the model used is a Badger airbrush, model 150™ (serial No. WE-150-4 PK) with nozzle sizes M and L. This Badger 150™ was coupled to a WE-Atlantis membrane air compressor, model TF 368, 220 volts and 135 watts.

Protecting/Retaining Layer Disintegration Test

This protecting/retaining layer was then dipped into a working medium and subjected to a force convection. These working media, in vitro, subjected to a force convection, make it possible to simulate in part the conditions encountered in vivo during the implantation of the implantable medical devices such as stents.

One of the parameters for measuring the hold and therefore the retaining force is the measurement of the rate of disintegration of this layer. The rate of disintegration of the retaining layer is directly linked to the rate of appearance of dexamethasone in the working medium. The concentration of dexamethasone is therefore monitored in the working medium as a function of time. The technique used to monitor the dexamethasone concentration as a function of time is high-performance liquid chromatography or HPLC.

Example 6-1

Working medium: No. 1 and No. 2
Surface material of the implant (stent): 316L stainless steel and 316L stainless steel coated with titanium oxynitride
Protecting/retaining layer: monolayer having a thickness of 0.1 to 20 microns, preferably approximately 12 microns
Composition of the protecting/retaining layer: 80% PEG 8000 20% dexamethasone
Protecting/retaining layer hold time: from 1 to 45 minutes, but preferably approximately 6 minutes (all configurations)

Example 6-2

Working medium: No. 1 and No. 2
Surface material of the implant (stent): 316L stainless steel and 316L stainless steel coated with titanium oxynitride
Protecting/retaining layer: monolayer having a thickness of 0.1 to 20 microns, but preferably 10 microns
Composition of the retaining layer: 67% PEG 8000 33% dexamethasone Protecting/retaining layer hold time: from 1 to 45 minutes, but preferably approximately 17 minutes (all configurations)

Example 6-3

Working medium: No. 1 and No. 2
Surface material of the implant (stent): 316L stainless steel and 316L stainless steel coated with titanium oxynitride
Protecting/retaining layer: monolayer having a thickness of 0.1 to 20 microns, but preferably 10 microns
Composition of the protecting/retaining layer: 34% PEG 8000 33%-PVP K30-33%-dexamethasone
Protecting/retaining layer hold time: from 1 to 45 minutes, but preferably approximately 12 minutes (all configurations)

Example 6-4

Working medium: No. 1 and No. 2
Surface material of the implant (stent): 316L stainless steel and 316L stainless steel coated with titanium oxynitride
Protecting/retaining layer: monolayer having a thickness of 0.1 to 20 microns, but preferably 10 microns
Composition of the protecting/retaining layer: 50% PEG 8000-50% dexamethasone
Protecting/retaining layer hold time: from 1 to 45 minutes, but preferably approximately 40 minutes (all configurations)

It is understood that, by virtue of the invention, it is possible to obtain a protecting/retaining layer, the disintegration rate of which can be adjusted on demand in order to enable controlled release of the active agent or of the medicament which will be deposited in a solid layer 36 on the implantable medical device 10 (or 20) before the protecting/retaining layer 38 itself is deposited. As previously indicated, it is the disintegration rate of the protecting/retaining layer which mainly adjusts the rate of release of the medicament or active ingredient deposited in a solid layer 36 on the implantable medical device, in particular in the microreservoirs or microcavities, insofar as the rate of dissolution or of administration of the medicament or active ingredient deposited in solid form in the microreservoirs or microcavities is dependent on the ability of the bloodstream to gain access to said solid deposit, which is protected via the application, under strong pressure, of the outside wall of the stent against the inside wall of the blood vessel in which it is inserted.

It is thus understood that the invention clearly makes it possible to solve all the technical problems stated above, in a simple, safe and reliable manner which can be used on the industrial and medical scale, and also to implement a method of treatment which provides a technical effect which is improved, unexpectedly, compared with the prior art.

The invention claimed is:

1. An implantable medical device to be implanted at a site of implantation, comprising at least one therapeutically active agent or medicament, comprising:
   receiving means for receiving at least a layer consisting essentially of said active agent or medicament, in the form of a solid deposit; and
   at least one biocompatible and biodegradable protecting/retaining layer for protecting the active agent or medicament until it is at its site of implantation, said biocompatible and biodegradable protecting/retaining layer comprising at least one biocompatible and biodegradable film-forming agent and at least one hydrophobic, biocompatible, agent in an amount sufficient to control the disintegration rate of the protecting/retaining layer.

2. The device of claim 1, wherein the biocompatible and biodegradable film-forming agent is selected from a polyalkylene glycol, a polyvinylpyrrolidone and mixtures thereof in any proportions.

3. The device of claim 2, wherein the polyalkylene glycol comprises or consists of polyethylene glycol.

4. The device of claim 1, wherein the hydrophobic agent comprises dexamethasone or a dexamethasone derivative.

5. The device of claim 4, wherein the dexamethasone derivative comprises dexamethasone, dexamethasone phosphate, dexamethasone acetate and any mixture thereof.

6. The device of claim 1, wherein the relative ratio by weight of the biocompatible and biodegradable film-forming agent to the hydrophobic agent varies between 99% and 1% of film-forming agent for 1% to 99% by weight of hydrophobic agent.

7. The device of claim 1 wherein the protecting/retaining layer comprises from 0.1 to 100 µg of dexamethasone per $mm^2$ of protecting/retaining layer surface.

8. The device of claim 1 wherein the implantable medical device comprises an internal surface and an external surface, and said receiving means for receiving the active agent or medicament are at least in part located on at least a part of the external surface which comprises surface sculpturing.

9. The device of claim 8, wherein the surface sculpturing comprises the formation of reservoirs defining a predetermined individual reservoir volume and enabling a predetermined volume or mass of active agent(s) or medicament(s) to be loaded.

10. The device of claim 9, characterized in that the reservoir formations are selected from the group comprising incisions, channels, wells or cavities, with closed bottoms of concave or non concave shape.

11. The device of claim 9 wherein the reservoir formations are of micrometric average size ranging between about 1 µm and about 600 µm.

12. The device of claim 1 wherein the implantable medical devices selected from the group consisting of a stent; a prosthesis; an orthopedic prosthesis; an implant; a dental implant; and a surgical thread or cord.

13. The device of claim 1, wherein the implantable medical device comprises a substrate and at least one ceramic coating layer with, optionally, at least one intermediate, nonporous, metallic adhesion layer.

14. The device of claim 1, wherein the implantable medical device comprises, on its external surface, a multitude of micro reservoirs, said active agent(s) or medicament(s) being deposited inside said micro reservoirs in the form of at least one solid deposit layer.

15. The device of claim 9, wherein said protecting/retaining layer is deposited at the external surface, in said reservoirs, on top of the solid deposit of said medicament(s) or active agent(s) to provide it with protection until it is at its site of implantation.

16. The device of claim 1, wherein said therapeutically active agent(s) or medicament(s) is water-soluble and comprises one or more cicatrization-promoting agent(s) in the form of a solid deposit; in an effective amount for inducing cicatrization or healing of injured tissues in the vicinity of the implantable medical device.

17. The device of claim 16, wherein the cicatrization-promoting agent comprises a non-reducing saccharide or a sulfated analog thereof.

18. The device of claim 16 wherein the cicatrization-promoting agent comprises a non-reducing disaccharide or a sulfated analog thereof.

19. The device of claim 16, wherein the cicatrization-promoting agent comprises sucrose or a sulfated analog thereof.

20. The device of claim 16, wherein the cicatrization-promoting agent comprises a monosaccharide or a sulfated analog thereof.

21. The device of claim 16, wherein the cicatrization-promoting agent comprises glucose or a sulfated analog thereof.

22. The device of claim 16, wherein the cicatrization-promoting agent comprises fructose or a sulfated analog thereof.

23. The device of claim 17, wherein the sulfated analog is in the form of a salt selected from a sodium salt, a potassium salt and mixtures thereof.

24. The device of claim 16, wherein the cicatrization-promoting agent comprises sodium sucrose octasulfate.

25. The device of claim 1, wherein the active agent or medicament is water-soluble and comprises at least one growth factor inhibitor in the form of a solid deposit.

26. The device of claim 25, wherein the growth factor inhibitor comprises octreotide, in the form of a solid deposit.

27. An implantable medical device to be implanted at a site of implantation, comprising at least one therapeutically active agent or medicament, comprising:
receiving means for receiving at least a layer consisting essentially of said active agent or medicament in the form of a solid deposit; and
at least one biocompatible and biodegradable protecting/retaining layer for protecting the active agent or medicament until it is at its site of implantation, said biocompatible and biodegradable protecting/retaining layer comprising at least one biocompatible and biodegradable film-forming agent and at least one hydrophobic, biocompatible, agent for controlling the disintegration rate of the protecting/retaining layer, wherein the active agent or medicament is water-soluble and comprises an NO precursor agent in the form of a solid deposit.

28. The device of claim 27, wherein the NO precursor agent is selected from L-arginine, L-lysine and mixtures thereof.

29. An implantable medical device to be implanted at a site of implantation, comprising at least one therapeutically active agent or medicament, comprising:
receiving means for receiving at least a layer consisting essentially of said active agent or medicament, in the form of a solid deposit; and
at least one biocompatible and biodegradable protecting/retaining layer for protecting the active agent or medicament until it is at its site of implantation, said biocompatible and biodegradable protecting/retaining layer comprising at least one biocompatible and biodegradable film-forming agent and at least one hydrophobic, biocompatible, agent for controlling the disintegration rate of the protecting/retaining layer, the device further comprising at least one additional therapeutic agent.

30. The device of claim 29, wherein said at least one additional therapeutic agent is an anti-restenosis agent.

31. The device of claim 30, wherein the anti-restenosis agent is selected from the group consisting of a medicament inhibiting smooth muscle cell proliferation, a cytoskeletal inhibitor, and a macrocyclictriene antibiotic.

32. An implantable medical device to be implanted at a site of implantation, comprising at least one therapeutically active agent or medicament, comprising receiving means for receiving at least a layer consisting essentially of said active agent or medicament, in the form of a solid deposit; and least one biocompatible and biodegradable protecting/retaining layer for protecting the active agent or medicament until it is at its site of implantation, said biocompatible and biodegradable protecting/retaining layer comprising at least one biocompatible and biodegradable film-forming agent selected from a polyalkylene glycol, a polyvinylpyrrolidone and mixtures thereof in any proportions, and at least one hydrophobic, biocompatible, agent in an amount sufficient to control the disintegration rate of the protecting/retaining layer comprising a dexamethasone component selected from dexamethasone, dexamethasone phosphate, disodium salt of dexamethasone phosphate, dexamethasone acetate, and any mixture thereof.

33. An implantable medical device to be implanted at a site of implantation, comprising at least one therapeutically active agent or medicament, comprising receiving means for receiving at least a layer consisting essentially of said active agent or medicament, in the form of a solid deposits and at least one biocompatible and biodegradable protecting/retaining layer for protecting the active agent or medicament until it is at its site of implantation, said biocompatible and biodegradable protecting/retaining layer comprising from 60% to 30% by weight of at least one biocompatible and biodegradable film-forming agent and from 40% to 70% by weight of at least one hydrophobic, biocompatible, agent for controlling the disintegration rate of the protecting/retaining layer.

34. An implantable medical device to be implanted at a site of implantation, comprising at least one therapeutically active agent or medicament, comprising receiving means for receiving at least a layer consisting essentially of said active agent or medicament, in the form of a solid deposit; and at least one biocompatible and biodegradable protecting/retaining layer for protecting the active agent or medicament until it is at its site of implantation, said biocompatible and biodegradable protecting/retaining layer comprising from 80% to 30% by weight of at least one biocompatible and biodegradable film-forming agent and from 20% to 70% by weight of at least one hydrophobic, biocompatible, agent for controlling the disintegration rate of the protecting/retaining layer.

* * * * *